US012288195B1

(12) United States Patent
Salud et al.

(10) Patent No.: US 12,288,195 B1
(45) Date of Patent: *Apr. 29, 2025

(54) SYSTEMS, METHODS AND APPARATUS TO PROCESS MEDICAL PRESCRIPTION ORDER REJECTIONS

(71) Applicant: WALGREEN CO., Deerfield, IL (US)

(72) Inventors: Lawrence Salud, Chicago, IL (US); Joseph Anthony Kuta, Highland Park, IL (US); Nicholas J. Leners, Round Lake, IL (US)

(73) Assignee: WALGREEN CO., Deerfield, IL (US)

( * ) Notice: Subject to any disclaimer, the term of this patent is extended or adjusted under 35 U.S.C. 154(b) by 196 days.

This patent is subject to a terminal disclaimer.

(21) Appl. No.: 17/897,046

(22) Filed: Aug. 26, 2022

Related U.S. Application Data

(63) Continuation of application No. 16/669,265, filed on Oct. 30, 2019, now Pat. No. 11,461,742.

(51) Int. Cl.
*G06Q 40/08* (2012.01)
*G06N 20/00* (2019.01)
*G06Q 20/02* (2012.01)
*G06Q 50/22* (2018.01)
*G16H 20/00* (2018.01)

(52) U.S. Cl.
CPC .......... *G06Q 20/023* (2013.01); *G06N 20/00* (2019.01); *G06Q 40/08* (2013.01); *G06Q 50/22* (2013.01); *G16H 20/00* (2018.01)

(58) Field of Classification Search
CPC ..................................................... G06Q 40/08
See application file for complete search history.

(56) References Cited

U.S. PATENT DOCUMENTS 10,331,855 B1 * 6/2019 Bratton .................. G16H 20/00

OTHER PUBLICATIONS

Microsoft Docs, "Mining Structures (Analysis Services—Data Mining)", Microsoft, 2018, https://docs.microsoft.com/en-us/sql/analysis-services/data-mining/mining-structures-analysis-services-data-mining?view=sql-server-2017, as downloaded on Sep. 5, 2019, 8 pages.

(Continued)

*Primary Examiner* — Edward Chang
(74) *Attorney, Agent, or Firm* — MARSHALL, GERSTEIN & BORUN LLP; Randall G. Rueth

(57) ABSTRACT

Example systems, methods and apparatus to process medical prescription order rejections are disclosed. An example computer-implemented method, executed by one or more processors, to process a medical prescription order rejection may include: submitting, using one or more processors, a first order for a medical prescription to a third-party entity for payment; and when a rejection of the first order is received from the third-party entity: processing, with a trained machine learning model, the first order to form a second order for the medical prescription, wherein the machine learning model is trained by one or more processors based on training data representing a plurality of rejected orders for prescriptions and a plurality of approved orders for prescriptions by updating the machine learning model based on computed differences between (i) orders for medical prescriptions determined by the machine learning model, and (ii) associated approved and rejected orders; and submitting, using one or more processors, the second order for the medical prescription to the third-party entity for payment.

20 Claims, 6 Drawing Sheets

(56) References Cited

OTHER PUBLICATIONS

Kelly et al., "The Last Mile: Operationalizing Data Science", Pivotal Software, Inc., 2017, https://content.pivotal.io/white-papers/the-last-mile-operationalizing-data-science, 12 pages.

* cited by examiner

SYSTEMS, METHODS AND APPARATUS TO PROCESS MEDICAL PRESCRIPTION ORDER REJECTIONS

CROSS-REFERENCE TO RELATED APPLICATIONS

This application is a continuation of U.S. patent application Ser. No. 16/669,265 entitled "Systems, Methods and Apparatus to Process Medical Prescription Order Rejections," filed on Oct. 30, 2019, the entire contents of which is hereby expressly incorporated herein by reference.

FIELD OF THE DISCLOSURE

This disclosure relates generally to medical prescriptions, and, more particularly, to systems, methods and apparatus to process medical prescription order rejections.

BACKGROUND

Prescribers (e.g., medical professionals) write medical prescriptions (medications, supplies, therapy, for example) for their patients. A supplier (e.g., a pharmacy) processes a prescription by submitting an order for the prescription item(s) to a third-party payor (an insurance company, a copay assistance entity, for example) who indicates whether or how much of the cost of the prescription item(s) will be covered by the patient's coverage. Any difference is due by the patient when the prescription item(s) are provided. In some instances, the third-party payor may reject the order partially or in whole for a variety of reasons.

Figure 1:
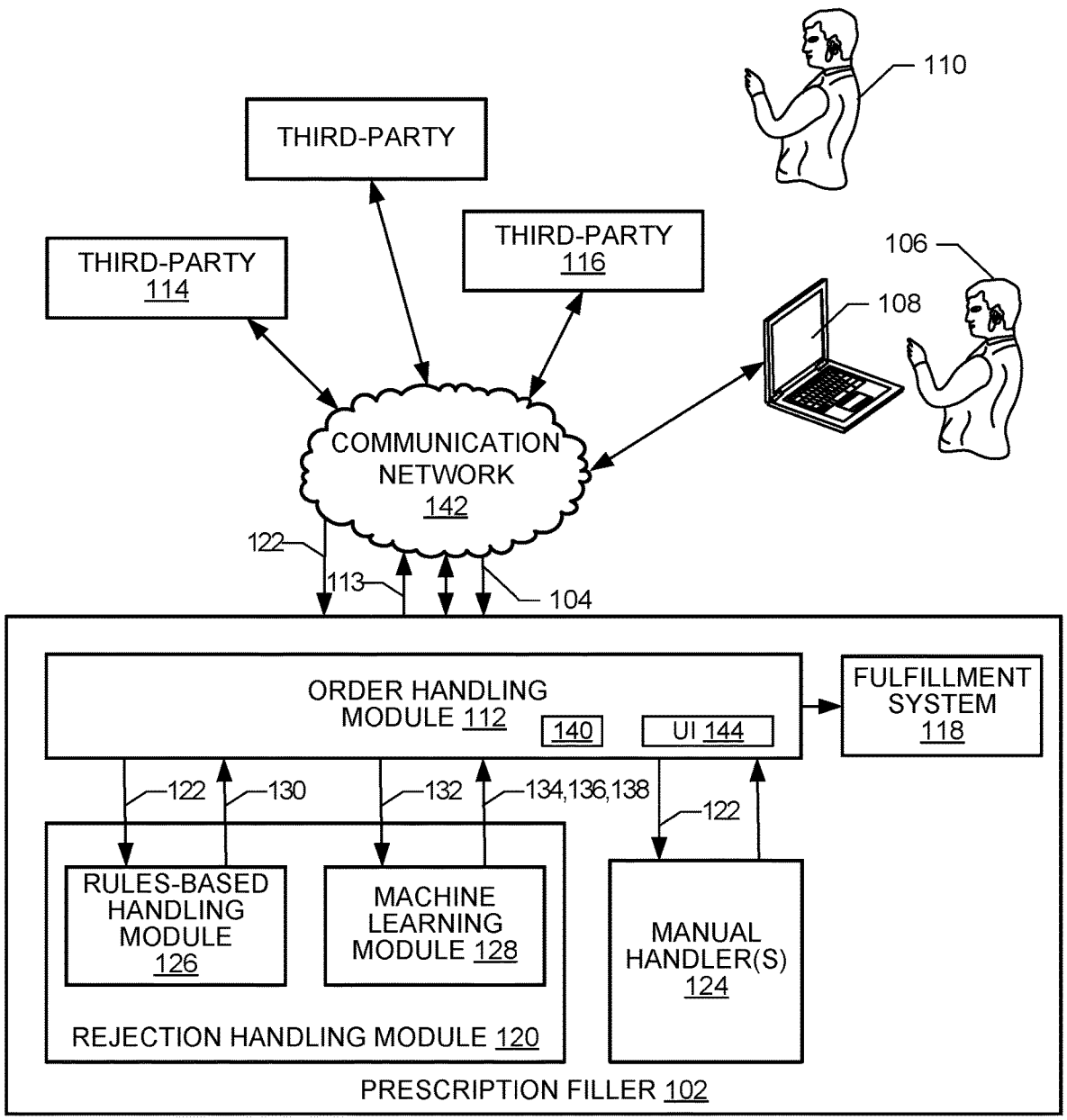
FIG. 1 is a block diagram of an example order rejection handler to resolve medical prescription order rejections, in accordance with aspects of this disclosure, and shown in an example environment of use.

The figures depict embodiments of this disclosure for purposes of illustration only. One skilled in the art will readily recognize from the following discussion that alternate embodiments of the structures and methods illustrated herein may be employed without departing from the principles set forth herein.

In general, the same reference numbers will be used throughout the drawing(s) and accompanying written description to refer to the same or like parts. The figures are not to scale. Connecting lines or connectors shown in the various figures presented are intended to represent example functional relationships and/or physical or logical couplings between the various elements.

DETAILED DESCRIPTION

Medical suppliers (e.g., pharmacies, home medical supply stores, hospitals, outpatient surgical offices, medical offices, dental offices, medical clinics, therapy offices, etc.) collectively spend tens of millions of hours manually handling orders for medical prescriptions (referred to simply prescriptions herein) that were rejected by a third-party, that is neither a patient nor a prescriber. Those rejections may be in part, in whole and/or may be for any number of reasons. For example: (a) a medication refill is being requested too soon; (b) an invalid coverage rejection when insurance coverage was not effective on the date that the prescription was submitted; (c) a drug not covered rejection when an insurance plan restricts the use of a specific medication or a type of medication; (d) a prior authorization rejection when an insurance plan does not allow the use of a medication without an evaluation of the patient's specific case or previous therapies attempted; (e) a non-matched plan rejection when there is missing information in the patient's insurance profile or their personal information profile; (f) a days supply rejection when the amount of medication billed exceeds the plan daily or monthly allowance for that medication; etc.

In some systems, when a rejection of a order by a third-party occurs, one or more pre-determined rules are applied that compare the indicated reason(s) for the rejection with known correction combinations. If a match is found, the order is accordingly modified on behalf of a medical supplier team member and resubmitted to the third-party. If no match is identified, the rejection is identified for manual handling. In an example using such rules-based adjustments, approximately 85% of initial order rejections were automatically corrected and subsequently approved. However, the remaining 15% of uncorrected orders can still represent a large amount of manual effort, thereby resulting in lost opportunities and less time spent in direct customer care.

To overcome these and/or other problems, systems, methods, apparatus, and articles of manufacture to process prescription order rejections are disclosed herein. In disclosed examples, machine learning is used to automatically modify, adjust, etc. an order for a prescription that has been previously rejected such that the modified order will be approved by a third-party. The machine learning models can be trained using past example orders that were rejected and then approved after either manual adjustment and/or adjustment based on one or more pre-determined rules. An example machine learning model is able to correct 6% to 13% of the initial rejections that could not be corrected using pre-determined rules. Together, 91% to 98% of initial rejections can be automatically modified using pre-determined rules and machine learning, re-submitted for approval, and filled, without manual interaction, thereby significantly reducing lost opportunity costs and significantly reducing time away from direct customer care.

A disclosed example computer-implemented method, executed by a processor, to process a prescription order rejection includes: submitting, using one or more processors, a first order for a prescription to a third-party entity for payment; when the first order is rejected by the third-party entity, processing, with a machine learning model, the first order to form a second order for the prescription; submitting, using one or more processors, the second order for the prescription to a third-party entity for payment; and when the second order is approved by the third-party entity, notifying, using one or more processors, a prescription fulfillment entity that the prescription can be fulfilled.

Example prescriptions include a prescription for a medication, a medical supply, a durable medical supply, a disposable medical supply, a medical therapy, or a dental supply. Example third-party entities include an insurance company, a primary insurance company, a secondary insurance company, a government institution, a co-pay assistance program, a co-pay assistance organization, or a manufacturer. Example prescription fulfillment entities include a pharmacy, a home medical supply store, a hospital, an outpatient surgical office, a medical office, a dental office, a medical clinic, or a medical therapy office.

For clarity of explanation, the examples disclosed herein will focus on prescription medications, however, they could be used to resolve prescription order rejections for any other medical items that may be prescribed. Moreover, while examples disclosed herein are described with respect to prescriptions for humans paid for by third-parties, it will be appreciated that the examples disclosed herein can be used for animals.

Reference will now be made in detail to non-limiting examples, some of which are illustrated in the accompanying drawings.

FIG. 1 is a diagram of an example system 100 to, among possibly other things, process prescription order rejections. The system 100 includes a prescription filler 102 (e.g., a pharmacy, etc.) to fill prescriptions 104 for medications. The prescriptions 104 may be received from any number or type(s) prescribers (e.g., a medical professional, a doctor, a nurse practitioner, a dentist, etc.) or representatives thereof, one of which is designated at reference numeral 106, via any number or type(s) of user devices (e.g., a facsimile, a laptop computer, a tablet, a smartphone, etc.), one of which is designated at reference numeral 108. While not shown in FIG. 1, prescriptions 104 may additionally or alternatively be physically mailed or faxed to, or physically dropped off at the prescription filler 102 by the prescriber 106 (or a representative thereof) or by a patient 110.

An order handling module 112 of the prescription filler 102 processes the prescription(s) 104 for the patient 110 by submitting orders 113 for the prescriptions 104 to the third-party payor(s) associated with the patient (two of which is designated at reference numeral 114 and 116). The prescription(s) 104 approved by the payor 114, 116 are sent to a fulfillment system 118 to prepare the prescription(s) 104 for the patient 110.

To automatically resolve order rejections, the example prescription filler 102 includes a order rejection handling module 120. The order rejection handling module 120 may be, or include a portion of a memory unit (e.g., the program memory 604 of FIG. 6) configured to store software, and machine- or computer-readable instructions that, when executed by a processing unit (e.g., the processor 602 of FIG. 6), cause the order rejection handling module 120 to attempt to automatically resolve a rejected order 122. When the order rejection handling module 120 is unable to automatically resolve the rejected order 122, the reject order 122 is routed to a manual order handler 124 (e.g., a pharmacy staff member) to attempt manual order rejection resolution. If the order rejection handling module 120 or the manual order handler 124 is able to resolve the order rejection, the prescription 104 is sent to the fulfillment system 118 to prepare the prescription(s) 104 for the patient 110. If the rejected order 122 cannot be automatically or manually resolved by, respectively, the order rejection handling module 120 or the manual order handler 124, the order handling module 112 may notify the prescriber 106 and/or the patient 110 that the prescription 104 cannot be filled.

To automatically resolve rejected orders, the order rejection handling module 120 includes a rules-based handling module 126 and a machine learning module 128. The rules-based handling module 124 identifies pre-determined rules that correspond to the reason(s) for the order rejection. If a match is identified, the rules-based handling module 126 modifies the rejected order 122 to form a modified order 130 based on the identified rule(s), sequentially or in combination, on behalf of a medical supplier team member, and the order handling module 112 submits the modified order 130 to the third-party 114, 116. If no match is identified or the modified order(s) 130 are rejected, the order rejection 122 is routed to the machine learning module 128 for further order rejection resolution.

An input vector 132 including order rejection reason information for the rejected order 122 (e.g., one or more rejection codes), prescription information for the rejected order (e.g., medication, quantity, prescription instruction(s), coverage information, ancillary information, etc.) and/or submitted order information are input to the machine learning module 128. The machine learning module 128 may be, or include a portion of a memory unit (e.g., the program memory 604 of FIG. 6) configured to store software, and machine- or computer-readable instructions that, when executed by a processing unit (e.g., the processor 602 of FIG. 6), cause the machine learning module 132 to execute a machine learning model to automatically resolve order rejections. In some examples, the machine learning module 132 implements gradient boosting machine learning, for example, using the open source eXtreme Gradient Boosting (XGBoost) algorithm. In some examples, the order handling module 112 forms the input vector 132. In other examples, the machine learning module 128 forms the input vector 132 from the prescription 104 and the rejected order 122.

Figure 2:
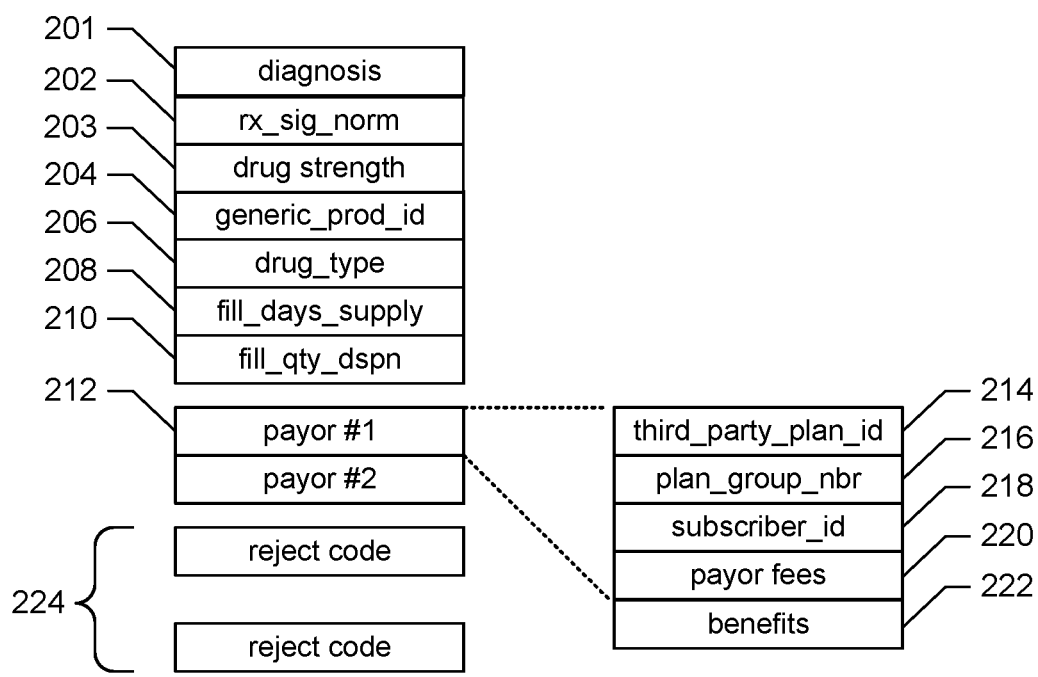
FIG. 2 is a block diagram of an example input vector for the machine learning model of FIG. 1.

An example input vector 132 to the machine learning module 126 is shown in FIG. 2. A diagnosis field 201 represents a medical diagnosis associated with the prescription. An rx_sign_norm field 202 represents usage information, i.e., how the medication is to be used (e.g., take 1 two times daily), a drug strength field 203 represents an amount of the medication per dose, a generic_prod_id field 204 provides information regarding generic equivalents, and a drug_type field 206 includes 14 characters that indicate drug group (e.g., decongestant), drug class (e.g., sympathomimetics), drug subclass (e.g., systemic decongestants), drug name (e.g., pseudoephedrine), drug name ext. (e.g., hydrochloride), dosage form (e.g., tablet) and strength (e.g., 60 mg). The input vector 132 further includes a fill_days_supply field 208 that indicates how many days are being supplied, and a fill_qty_dspn field 210 that indicates how many are being dispensed. The input vector 132 also includes payor information 212 for one or more payors. The payor information 212 includes a third party_plan_id field 214 that represents the payor, a plan_group_nbr field 216 that identifies a patient's plan, a subscriber_id field 218 that identifies an insured of the plan, fees associated with the payor are stored in a fees field 220, and a benefits field 222 contains benefits information. The input vector additionally includes one or more order rejection codes 224. While an example machine learning engine input vector 132 is shown in FIG. 2, the fields shown in FIG. 2 may be combined, divided, re-arranged, omitted, eliminated or implemented in any other way. Further, the input vector 132 may include one or more fields, entries, parameters, values in addition to, or instead of those illustrated in FIG. 2, or may include more than one of any or all of the illustrated fields, entries, parameters and values.

Returning to FIG. 1, the machine learning module 128 processes the input vector 132, thereby forming an output 134 that represents a modified order 136 and/or represents information 138 that the order handling module 112 can process to form a modified order 140. The order handling module 112 submits the modified order 136, 140 to the third-party payor(s) 114, 116. If the modified order 136, 140 is approved by the third-party payor(s) 114, 116, the order handling module 112 sends the prescription 104 to the fulfillment system 118 to prepare the prescription(s) 104 for the patient 110. If the modified order 136, 140 is not approved by the third-party payor(s) 114, 116, the order rejection 122 is routed to the manual order handler(s) 124 for manual processing.

The prescription filler 102, the laptop 108 and the third-party payor(s) 114, 116, may be communicatively coupled via any number or type(s) of communication network(s) 142. The communication network(s) include, but are not limited to, the Internet, a local area network (LAN), a metropolitan area network (MAN), a wide area network (WAN), a mobile, a wired network, a Wi-Fi® network, a cellular network, a wireless network, a private network, a virtual private network, etc.

In some examples, the order handling module 112 implements one or more user interfaces 144 (UI) (e.g., a web-based interface) that can be used by the manual order handler(s) 124 or other persons such as medical supplier team members to manually resolve order rejections.

While the example prescription filler 102 and/or, more generally, the example system 100 to resolve rejected orders are illustrated in FIG. 1, one or more of the elements, processes and devices illustrated in FIG. 1 may be combined, divided, re-arranged, omitted, eliminated or implemented in any other way. The order handling module 112, the order rejection handling module 120, the rules-based handling module 126, the machine learning module 128 and/or, more generally, the prescription filler 120 may be implemented by hardware, software, firmware and/or any combination of hardware, software and/or firmware. Thus, for example, any of the order handling module 112, the order rejection handling module 120, the rules-based handling module 126, the machine learning module 128 and/or, more generally, the prescription filler 102 could be implemented by one or more of an analog or digital circuit, a logic circuit, a programmable processor, a programmable controller, a graphics processing unit (GPU), a digital signal processor (DSP), an application specific integrated circuit (ASIC), a programmable logic device (PLD), a field programmable gate array (FPGA), a field programmable logic device (FPLD), etc. Moreover, the prescription filler 102 and/or, more generally, the system 100 may include one or more elements, processes or devices in addition to or instead of those illustrated in FIG. 1, or may include more than one of any or all of the illustrated elements, processes and devices. For example, while not shown for clarity of illustration, the prescription filler 102 of FIG. 1 may include various hardware components (e.g., a processor such as the processor 602 of FIG. 6, a server, a workstation, a distributed computing system, a GPU, a DSP, etc.) that may execute software, and machine- or computer-readable instructions to estimate costs of prescriptions. The prescription filler 102 also includes data communication components for communicating between devices.

Figure 3:
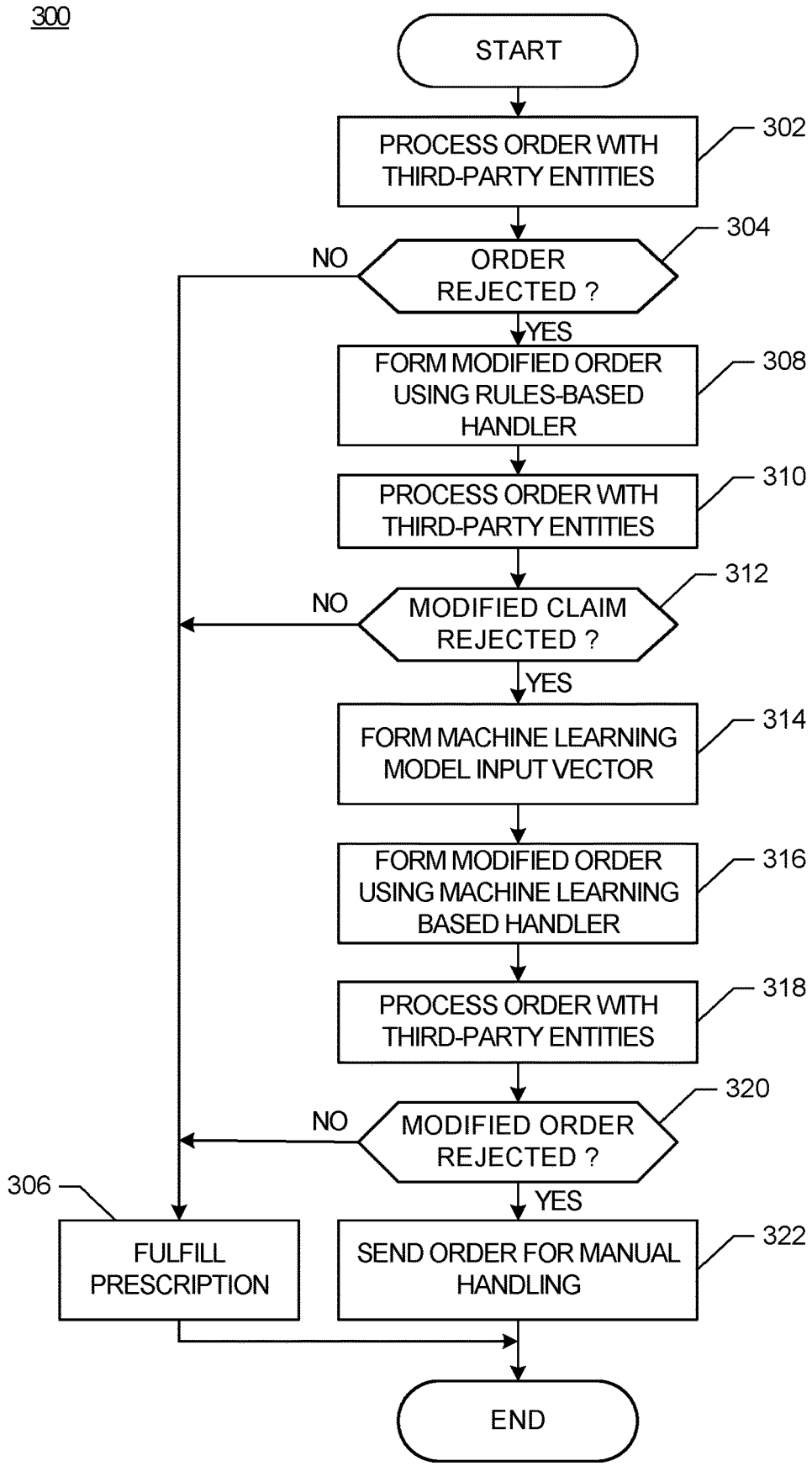
FIG. 3 is a flowchart representative of example method, hardware logic and instructions for implementing the order rejection handler of FIG. 1.

A flowchart 300 representative of example processes, methods, software, computer- or machine-readable instructions, etc. for implementing the prescription filler 120 is shown in FIG. 3. The processes, methods, software and instructions may be an executable program or portion of an executable program for execution by a processor such as the processor 602 of FIG. 6. The program may be embodied in software or instructions stored on a non-transitory computer- or machine-readable storage medium such as a compact disc (CD), a compact disc read-only memory (CD-ROM), a hard disk drive (HDD), a solid state drive (SDD), a digital versatile disk (DVD), a Blu-ray disk, a cache, a flash memory, a read-only memory (ROM), a random access memory (RAM), or any other storage device or storage disk associated with the processor 602 in which information is stored for any duration (e.g., for extended time periods, permanently, for brief instances, for temporarily buffering, and/or for caching of the information). Further, although the example program is described with reference to the flowchart illustrated in FIG. 3, many other methods of implementing the prescription filler 102 may alternatively be used. For example, the order of execution of the blocks may be changed, and/or some of the blocks described may be changed, eliminated, or combined. Additionally, or alternatively, any or all of the blocks may be implemented by one or more of a hardware circuit (e.g., discrete and/or integrated analog and/or digital circuitry), an ASIC, a PLD, an FPGA, an FPLD, etc. structured to perform the corresponding operation without executing software or instructions.

The example process of FIG. 3 begins with the order handling module 112 submitting a order 113 for a prescription 104 to the third-party payor(s) 114, 116 (block 302). If the order 113 is approved (block 304), the prescription 104 is sent to the fulfillment system 118 for fulfillment (block 306) and control exits from the example process of FIG. 3.

Returning to block 304, if the order 113 is rejected (block 304), the rules-based handling module 126 applies one or more pre-determined rules to the rejected order 122 to form a modified order 113 (block 308), and the order handling module 112 submits the rules-based modified order 113 to the third-party payor(s) 114, 116 (block 310). If the rules-based modified order 113 is approved (block 312), the prescription 104 is sent to the fulfillment system 118 for fulfillment (block 306) and control exits from the example process of FIG. 3.

Returning to block 312, if the modified order 113 is rejected (block 312), the machine learning module 128 and/or the order handling module 112 forms an input vector 132 from the prescription 104 and the order rejection 122 (block 314). The machine learning module processes the input vector to form a machine-learning modified order 113 (block 316), and the order handling module 112 submits the machine-learning modified order 113 to the third-party payor(s) 114,116 (block 318). If the machine-learning modified order 113 is approved (block 320), the prescription 104 is sent to the fulfillment system 118 for fulfillment (block 306) and control exits from the example process of FIG. 3.

Returning to block 320, if the machine-learning modified order 113 is rejected (block 320), the prescription 104 is sent to the manual order handler(s) 124 for manual handling (block 322) and control exits from the example process of FIG. 3.

Figure 4:
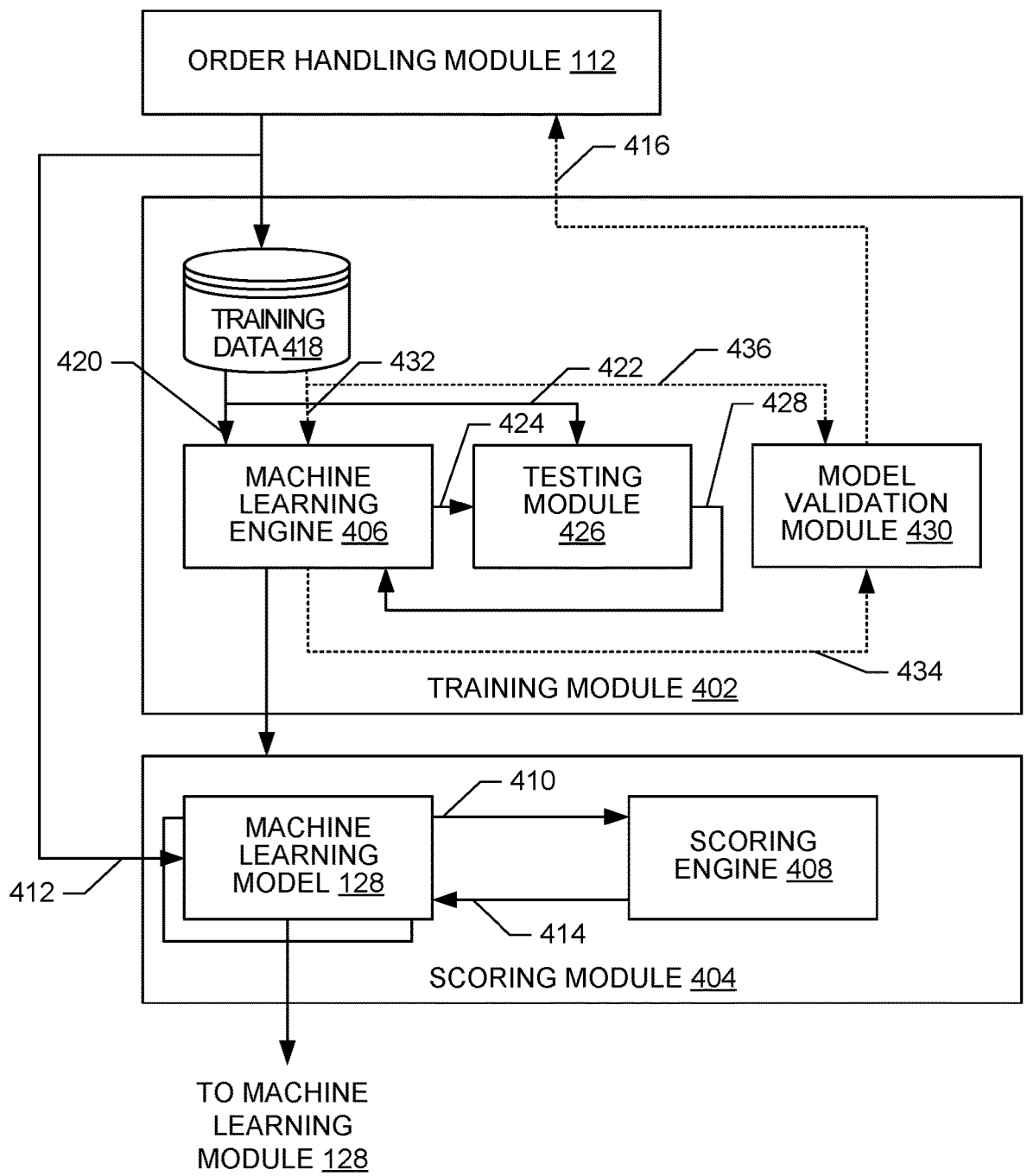
FIG. 4 is a block diagram of an example machine learning training module to train the machine learning module of FIG. 1, in accordance with teachings of this disclosure.

FIG. 4 is a block diagram of an example machine learning training module 400 having a training module 402 and a scoring module 404. The training module 402 includes a machine learning engine 406 for training a machine learning module. The scoring module 404 scores a final machine leaning model 128. Both the training module 402 and the scoring module 404 can be executed for use as the machine learning module 128 of FIG. 1. There can be one or more machine learning models 128 for scoring within the scoring module 404. The training module 402 and the scoring module 404 may be, or include a portion of a memory unit (e.g., the program memory 604 of FIG. 6) configured to store software, and machine- or computer-readable instructions that, when executed by a processing unit (e.g., the processor 602 of FIG. 6), cause the training module 402 to train, test and validate a machine learning model 128 from the machine learning engine 406, and cause the scoring module 404 to provide machine-language modified orders 136 to the scoring engine 408 or the order handling module 112. The scoring engine 408 is used to simulate using application programming interface (API) messaging such as RESTful API requests 410 to simulate requests 412 for modified orders 136, and RESTful API responses 414 to simulate the delivery 416 of modified orders 136. The scoring module 404 is used to facilitate this messaging and manage the machine learning model 128 such that the machine learning training module 400 can operate within the system 100 of FIG. 1.

The machine learning training module 400 includes a database of training data 418 that stores prescriptions 420, and corresponding approved and rejected orders 122 were approved or rejected on any number or type(s) of non-transitory computer- or machine-readable storage medium or disk using any number or type(s) of data structures.

As used herein, a non-transitory computer- or machine-readable storage medium or disk may be, but is not limited to, one or more of an HDD, an optical storage drive, a solid-state storage device, an SSD, a ROM, a RAM, a CD, a CD-ROM, a DVD, a Blu-ray disk, a cache, a flash memory, or any other storage device or storage disk in which information may be stored for any duration (e.g., permanently, for an extended time period, for a brief instance, for temporarily buffering, for caching of the information, etc.).

Input vectors 132 are formed for the prescriptions 420 and passed through the machine learning engine 406 to form trial modified orders 424. In the illustrated example of FIG. 4, the developing machine learning model within the machine learning engine 406 is trained using supervised learning. Accordingly, a testing module 426, which may be, or include a portion of a memory unit (e.g., the program memory 604 of FIG. 6) configured to store software, and machine- or computer-readable instructions that, when executed by a processing unit (e.g., the processor 602 of FIG. 6), cause the testing module 426 to compare the modified orders 424 determined by the machine learning engine 406 for the prescriptions 420 with the actual rejected and approved orders for the prescriptions 420 to form errors 428 that are used to develop and update the machine learning engine 406. The machine learning engine 406 develops, deploys and updates the final machine learning model 128 using, for example, gradient boosting machine learning, for example, using the open source eXtreme Gradient Boosting (XG-Boost)) algorithm, a neural network, deep learning, a regression technique, etc.

To validate the developing machine learning model within the machine learning engine 406, the training module 402 includes a model validation module 430. The model validation module 430 may be, or include a portion of a memory unit (e.g., the program memory 604 of FIG. 6) configured to store software, and machine- or computer-readable instructions that, when executed by a processing unit (e.g., the processor 602 of FIG. 6), cause the model validation module 430 to statistically validate the developing machine learning model using k-fold cross-validation. The data 418 is randomly split into k parts. The developing machine learning model is trained using k−1 of the k parts of the data 418 to form the modified orders 420. The machine learning module 126 is evaluated using the remaining 1 (one) part of the data 418 to form the modified orders 432, which the machine learning engine 406 has not been exposed to. Outputs 434 of the developing machine learning model for the prescriptions 432 are compared to actual rejected and approved orders 436 for the prescriptions 432 by the model validation module 430 to determine the performance or convergence of developing machine learning model. Performance or convergence can be determined by, for example, identifying when a metric computer over the errors 428 (e.g., a mean-square metric, a rate-of-decrease metric, etc.) satisfies a criteria (e.g., a metric is less than a predetermined threshold, such as a root mean squared error).

In some examples, the developing machine learning model within the machine learning engine 406 is initially trained using historical prescription and sold price data. The machine learning engine 406 may then deploy one or more new or updated machine learning models as new orders are processed. For example, deploying a machine learning model 128 running in parallel with the machine learning engine 406 can used to modify rejected orders. Periodically or aperiodically, the machine learning model 128 can be updated from the parallel machine learning engine 406. In addition, for example, the machine learning model 128 can be deployed as one or more MLeap model formats to perform scoring within the scoring module 404 and can provide these modified orders 136 in the form of predictions. MLeap is an open source serialization format and execution engine for machine learning pipelines, The MLeap format enables productionalization and scaling on a Docker container, Kubernetes cluster or similar. Similarly, predictions could be recorded and compared with post-training results to improve cost estimate prediction. Other deployable model formats may include PMML, Onyx, PFA, pickle, etc.

While the training module 402, the scoring module 404 and/or, more generally, the machine learning training module 400 to modify orders to resolve order rejections are illustrated in FIG. 4, one or more of the elements, processes and devices illustrated in FIG. 4 may be combined, divided, re-arranged, omitted, eliminated or implemented in any other way. The training module 402, the scoring module 404, the machine learning engine 406, the scoring engine 408, the testing module 426, the model validation module 430 and/or, more generally, the machine learning training module 400 may be implemented by hardware, software, firmware and/or any combination of hardware, software and/or firmware. Thus, for example, any of the training module 402, the scoring module 404, the machine learning engine 406, the scoring engine 408, the testing module 426, the model validation module 430 and/or, more generally, the machine learning training module 400 could be implemented by one or more of an analog or digital circuit, a logic circuit, a programmable processor, a programmable controller, a GPU, a DSP, an ASIC, a PLD, an FPGA, an FPLD, etc. Moreover, the machine learning training module 400 may include one or more elements, processes or devices in addition to or instead of those illustrated in FIG. 4, or may include more than one of any or all of the illustrated elements, processes and devices. For example, while not shown for clarity of illustration, the machine learning training module 400 of FIG. 4 may include various hardware components (e.g., a processor such as the processor 602 of FIG. 6, a server, a workstation, a distributed computing system, a GPU, a DSP, etc.) that may execute software, and machine- or computer-readable instructions to estimate costs of prescriptions. The machine learning training module 400 also includes data communication components for communicating between devices.

Figure 5:
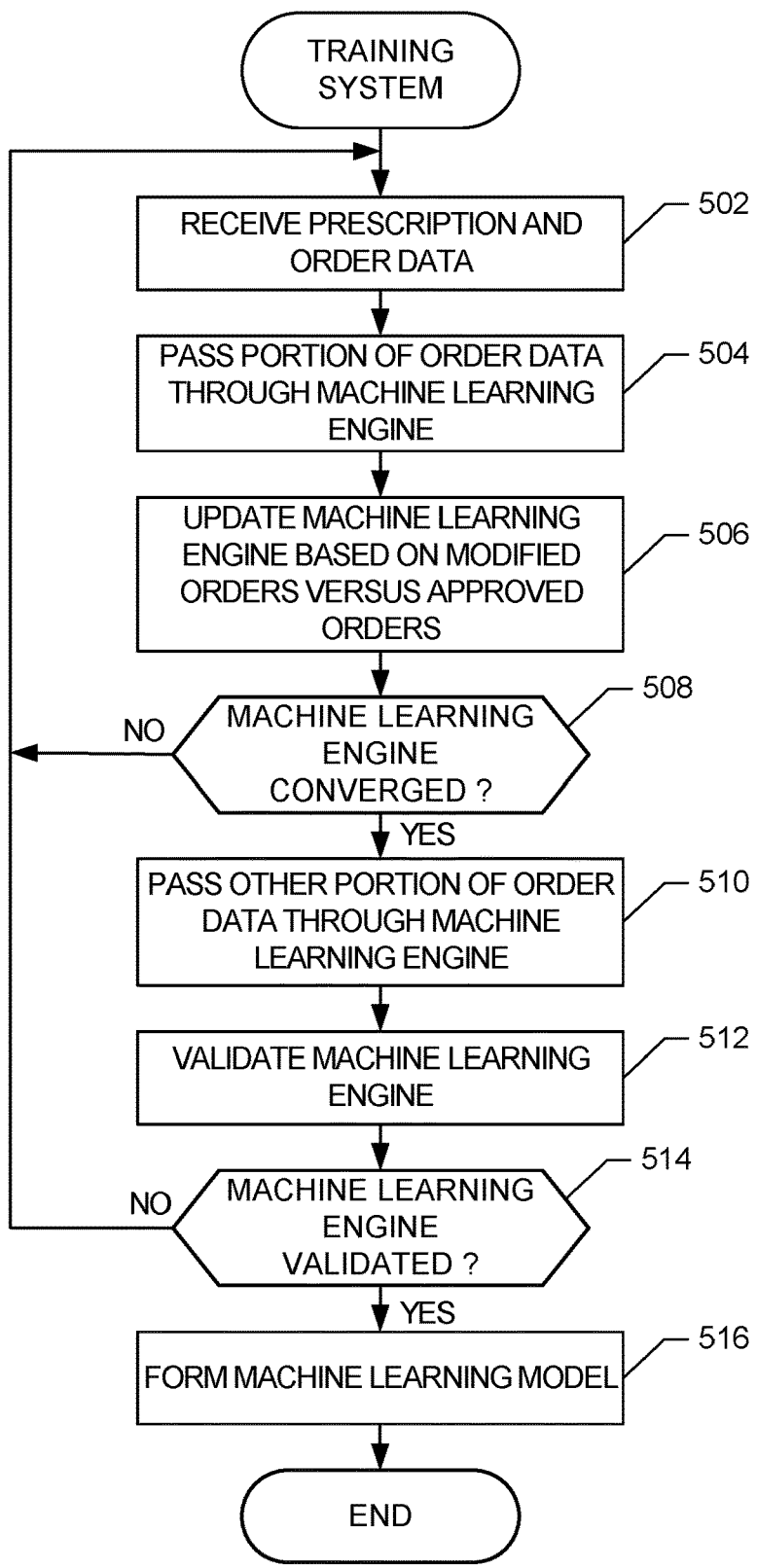
FIG. 5 is a flowchart representative of example method, hardware logic and instructions for implementing the machine learning training module of FIG. 4.

A flowchart 500 representative of example processes, methods, software, firmware, and computer- or machine-readable instructions for implementing the machine-learning training module 400 is shown in FIG. 5. The processes, methods, software and instructions may be an executable program or portion of an executable program for execution by a processor such as the processor 602 of FIG. 6. The program may be embodied in software or instructions stored on a non-transitory computer- or machine-readable storage medium or disk associated with the processor 602. Further, although the example program is described with reference to the flowchart illustrated in FIG. 5, many other methods of implementing the machine learning training module 400 may alternatively be used. For example, the order of execution of the blocks may be changed, and/or some of the blocks described may be changed, eliminated, or combined. Additionally, or alternatively, any or all of the blocks may be implemented by one or more hardware circuits (e.g., discrete and/or integrated analog and/or digital circuitry, an ASIC, a PLD, an FPGA, an FPLD, a logic circuit, etc.) structured to perform the corresponding operation without executing software or firmware.

The example process of FIG. 5 begins with receiving prescriptions, order approvals and order rejections, and storing them in the training data database 418 (block 502). Orders 432 and of the k−1 of k portions of the data 418 are passed through the machine learning engine 406 (block 504), and the machine learning engine 406 is updated based on comparisons by the testing module 426 of the outputs 424 of the machine learning engine 406 and approved orders 436 for the prescriptions 418 of the k−1 portions of the data 408 (block 506). If training of the machine learning engine 406 has not converged (block 508), control returns to block 504 to continue training the machine learning engine 406. If training of the machine learning engine 406 has converged (block 508), the orders 432 of the remaining portion of the data 418 are passed through the machine learning engine 406 (block 510), and outputs 434 of the machine learning engine 406 are used by the model validation module 430 to validate the machine learning engine 406 (block 512). If the machine learning engine 406 validates (block 514), the machine learning engine 406 is used to form the machine learning module 128 (block 516) (e.g., coefficients are copied, etc.), and control exits from the example process of FIG. 5. Otherwise, if the machine learning engine 406 does not validate (block 514), then control returns to block 502 to continue training.

As mentioned above, the example processes of FIGS. 3 and 5 may be implemented using executable instructions (e.g., computer and/or machine-readable instructions) stored on a non-transitory computer and/or machine-readable medium such as a hard disk drive, a flash memory, a read-only memory, a CD, a CD-ROM, a DVD, a cache, a random-access memory and/or any other storage device or storage disk in which information is stored for any duration (e.g., for extended time periods, permanently, for brief instances, for temporarily buffering, and/or for caching of the information). As used herein, the term non-transitory computer-readable medium is expressly defined to include any type of computer-readable storage device and/or storage disk and to exclude propagating signals and to exclude transmission media.

Figure 6:
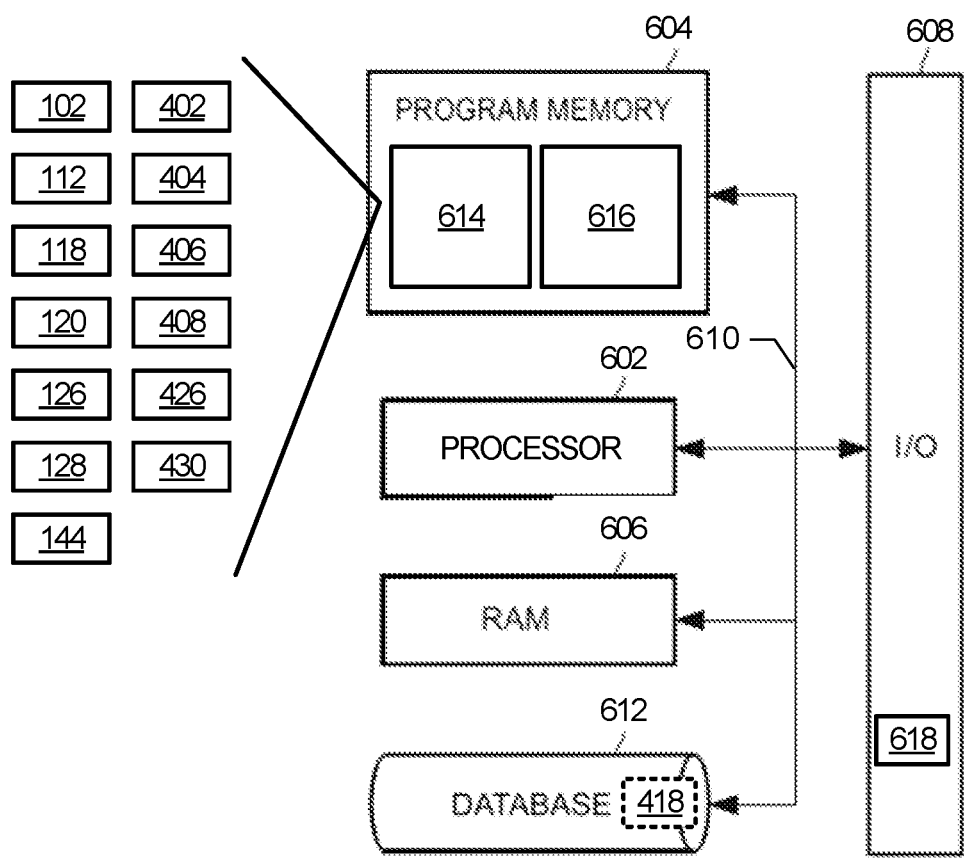
FIG. 6 is a block diagram of an example computing system to implement the various user interfaces, methods, functions, etc., to resolve prescription payment rejections, in accordance with aspects of this disclosure.

Referring now to FIG. 6, a block diagram of an example computing system 600 to resolve order rejections, in accordance with described embodiments. The example computing system 600 may be used to, for example, implement all or part of the prescription filler 102, the order handling module 112, the fulfillment system 118, the order rejection handling module 120, the rules-based handling module 126, the machine learning module 128, the UI 144, the training module 402, the scoring module 404, the machine learning module 406, the scoring engine 408, the testing module 426, and the model validation module 430. The computing system 600 may be, for example, a server, a personal computer, a workstation, a self-learning machine (e.g., a neural network), a mobile device (e.g., a cell phone, a smart phone, a tablet such as an IPAD™), a personal digital assistant (PDA), an Internet appliance, a DVD player, a CD player, a digital video recorder, a Blu-ray player, a gaming console, a personal video recorder, a set top box, a headset or other wearable device, or any other type of computing device The computing system 600 includes a processor 602, a program memory 604, a RAM 606, and an input/output (I/O) circuit 608, all of which are interconnected via an address/data bus 610. The program memory 604 may store software, and machine- or computer-readable instructions, which may be executed by the processor 602.

It should be appreciated that although FIG. 6 depicts only one processor 602, the computing system 600 may include multiple processors 602. Moreover, different portions of the system 100 and/or the machine learning training module 400 may be implement by different computing systems such as the computing system 600. The processor 602 of the illustrated example is hardware, and may be a semiconductor based (e.g., silicon based) device. Example processors 602 include a programmable processor, a programmable controller, a graphics processing unit (GPU), a digital signal processor (DSP), an ASIC, a PLD, an FPGA, an FPLD, etc. In this example, the processor 602 implements all or part of the prescription filler 102, the order handling module 112, the fulfillment system 118, the order rejection handling module 120, the rules-based handling module 126, the machine learning module 128, the UI 144, the training module 402, the scoring module 404, the machine learning module 406, the scoring engine 408, the testing module 426, and the model validation module 430.

The program memory 604 may include volatile and/or non-volatile memories, for example, one or more RAMs (e.g., a RAM 614) or one or more program memories (e.g., a ROM 616), or a cache (not shown) storing one or more corresponding software, and machine- or computer-instructions. For example, the program memory 604 stores software, machine- or computer-readable instructions, or machine- or computer-executable instructions that may be executed by the processor 602 to implement all or part of the prescription filler 102, the order handling module 112, the fulfillment system 118, the order rejection handling module 120, the rules-based handling module 126, the machine learning module 128, the UI 144, the training module 402, the scoring module 404, the machine learning module 406, the scoring engine 408, the testing module 426, and the model validation module 430. Modules, systems, etc. instead of and/or in addition to those shown in FIG. 6 may be implemented. The software, machine-readable instructions, or computer-executable instructions may be stored on separate non-transitory computer- or machine-readable storage mediums or disks, or at different physical locations.

Example memories 604, 614, 616 include any number or type(s) of volatile or non-volatile non-transitory computer- or machine-readable storage medium or disk, such as a semiconductor memories, magnetically readable memories, optically readable memories, hard disk drive (HDD), an optical storage drive, a solid-state storage device, a solid-state drive (SSD), a read-only memory (ROM), a random-access memory (RAM), a compact disc (CD), a compact disc read-only memory (CD-ROM), a digital versatile disk (DVD), a Blu-ray disk, a redundant array of independent disks (RAID) system, a cache, a flash memory, or any other storage device or storage disk in which information may be stored for any duration (e.g., permanently, for an extended time period, for a brief instance, for temporarily buffering, for caching of the information, etc.).

As used herein, the term non-transitory computer-readable medium is expressly defined to include any type of computer-readable storage device and/or storage disk and to exclude propagating signals and to exclude transmission media. As used herein, the term non-transitory machine-readable medium is expressly defined to include any type of machine-readable storage device and/or storage disk and to exclude propagating signals and to exclude transmission media.

In some embodiments, the processor 602 may also include, or otherwise be communicatively connected to, a database 612 or other data storage mechanism (one or more hard disk drives, optical storage drives, solid state storage devices, CDs, CD-ROMs, DVDs, Blu-ray disks, etc.). In the illustrated example, the database 612 stores the database of training data 418.

Although FIG. 6 depicts the I/O circuit 608 as a single block, the I/O circuit 608 may include a number of different types of I/O circuits or components that enable the processor 602 to communicate with peripheral I/O devices. Example interface circuits 608 include an Ethernet interface, a universal serial bus (USB), a Bluetooth® interface, a near field communication (NFC) interface, and/or a PCI express interface. The peripheral I/O devices may be any desired type of I/O device such as a keyboard, a display (a liquid crystal display (LCD), a cathode ray tube (CRT) display, a light emitting diode (LED) display, an organic light emitting diode (OLED) display, an in-place switching (IPS) display, a touch screen, etc.), a navigation device (a mouse, a trackball, a capacitive touch pad, a joystick, etc.), a speaker, a microphone, a printer, a button, a communication interface, an antenna, etc.

The I/O circuit 608 may include any number of network transceivers 618 that enable the computing system 600 to communicate with other computer systems or components that implement other portions of the system 100 or the machine learning training module 400 via, e.g., a network (e.g., the Internet). The network transceiver 618 may be a wireless fidelity (Wi-Fi) transceiver, a Bluetooth transceiver, an infrared transceiver, a cellular transceiver, an Ethernet network transceiver, an asynchronous transfer mode (ATM) network transceiver, a digital subscriber line (DSL) modem, a dialup modem, a satellite transceiver, a cable modem, etc.

Example systems, methods, apparatus, and articles of manufacture to process medical prescription order rejections are disclosed herein. Further examples and combinations thereof include at least the following.

Example 1 is a computer-implemented method, executed by one or more processors, to process a medical prescription order rejection, the method comprising: submitting, using one or more processors, a first order for a medical prescription to a third-party entity for payment; when the first order is rejected by the third-party entity, processing, with a machine learning model, the first order to form a second order for the medical prescription; submitting, using one or more processors, the second order for the medical prescription to the third-party entity for payment; and when the second order is approved by the third-party entity, notifying, using one or more processors, a prescription fulfillment entity that the medical prescription is available to be fulfilled.

Example 2 is the method of example 1, wherein the second order is submitted to a first third-party entity different from a second third-party entity the first order is submitted to.

Example 3 is the method of example 1 or example 2, further including, prior to forming the second order for the medical prescription: applying a plurality of rules to the first order to form a third order for the medical prescription; and submitting the third order for the medical prescription to the third-party entity for payment, wherein the first order is processed with the machine learning model to form the second order when the third order is rejected by the third-party entity.

Example 4 is the method of any of examples 1 to 3, further including, when the third order for the medical prescription is approved, notifying the prescription fulfillment entity that the medical prescription is available to be fulfilled.

Example 5 is the method of any of examples 1 to 4, further comprising, when the second order is rejected, submitting the first order for manual review.

Example 6 is the method of any of example 1 to 5, further comprising training the machine learning model with data representing a plurality of rejected orders and respective ones of a plurality of approved orders.

Example 7 is the method of example 6, further comprising: training the machine learning model with a first portion of the data; and validating the machine learning model with a second portion of the data.

Example 8 is the method of example 6, wherein the plurality of approved orders includes at least one of a third order generated by applying a plurality of rules, or a fourth order generated by manual review.

Example 9 is the method of any of examples 1 to 8, wherein the third-party entity includes at least one of an insurance company, a primary insurance company, a secondary insurance company, a government institution, a co-pay assistance program, a co-pay assistance organization, or a manufacturer.

Example 10 is a prescription filler system, the system comprising: a first interface configured to receive a medical prescription; a second interface to a third-party entity configured to submit a first order for the medical prescription to the third-party entity for approval; a machine learning model configured to form a second order for the medical prescription when the first order is rejected by the third-party entity, wherein the second interface is configured to submit the second order for the medical prescription to the third-party entity for payment; and a fulfillment system configured to fill the medical prescription when the second order is approved.

Example 11 is the system of example 10, wherein the first interface includes the second interface.

Example 12 is the system of example 10 or example 11, further including a rules-based handler configured to apply a plurality of rules to the first order to form a third order for the medical prescription, wherein the second interface is configured to submit the third order for the medical prescription to the third-party entity for payment, and wherein the first order is processed with the machine learning model to form the second order when the third order is rejected by the third-party entity.

Example 13 is the system of example 12, wherein the fulfillment system is configured to fill the medical prescription when the second third is approved.

Example 14 is the system of any of examples 10 to 13, wherein the third-party entity includes at least one of an insurance company, a primary insurance company, a secondary insurance company, a government institution, a co-pay assistance program, a co-pay assistance organization, or a manufacturer.

Example 15 is a non-transitory computer-readable storage medium comprising instructions that, when executed, cause a machine to: submit a first order for a medical prescription to a third-party entity for payment; when the first order is rejected by the third-party entity, process, with a machine learning model, the first order to form a second order for the medical prescription; submit the second order for the medical prescription to a third-party entity for payment; and when the second order is approved by the third-party entity, notify a prescription fulfillment entity that the medical prescription is available to be fulfilled.

Example 16 is the non-transitory computer-readable storage medium of example 15, including further instructions that, when executed, cause the machine to, prior to forming the second order for the medical prescription: apply a plurality of rules to the first order to form a third order for the medical prescription; and submit the third order for the medical prescription to the third-party entity for payment, wherein the first order is processed with the machine learning model to form the second order when the third order is rejected by the third-party entity.

Example 17 is the non-transitory computer-readable storage medium of example 15 or example 16, including further instructions that, when executed, cause the machine to, when the third order for the medical prescription is approved, notify the prescription fulfillment entity that the medical prescription is available to be fulfilled.

Example 18 is the non-transitory computer-readable storage medium of any of examples 15 to 17, including further instructions that, when executed, cause the machine to, when the second order is rejected, submit the first order for manual review.

Example 19 is the non-transitory computer-readable storage medium of any of examples 15 to 18, including further instructions that, when executed, cause the machine to train the machine learning model with data representing a plurality of rejected orders and respective ones of a plurality of approved orders.

Example 20 is the non-transitory computer-readable storage medium of example 19, including further instructions that, when executed, cause the machine to train the machine learning model with data representing a plurality of rejected orders and respective ones of a plurality of approved orders.

Example 21 is the non-transitory computer-readable storage medium of any of examples 15 to 20, wherein the third-party entity includes at least one of an insurance company, a primary insurance company, a secondary insurance company, a government institution, a co-pay assistance program, a co-pay assistance organization, or a manufacturer.

Use of "a" or "an" are employed to describe elements and components of the embodiments herein. This is done merely for convenience and to give a general sense of the description. This description, and the orders that follow, should be read to include one or at least one and the singular also includes the plural unless it is obvious that it is meant otherwise. A device or structure that is "configured" in a certain way is configured in at least that way, but may also be configured in ways that are not listed.

Further, as used herein, the expressions "in communication," "coupled" and "connected," including variations thereof, encompasses direct communication and/or indirect communication through one or more intermediary components, and does not require direct mechanical or physical (e.g., wired) communication and/or constant communication, but rather additionally includes selective communication at periodic intervals, scheduled intervals, aperiodic intervals, and/or one-time events. The embodiments are not limited in this context.

Further still, unless expressly stated to the contrary, "or" refers to an inclusive or and not to an exclusive or. For example, "A, B or C" refers to any combination or subset of A, B, C such as (1) A alone, (2) B alone, (3) C alone, (4) A with B, (5) A with C, (6) B with C, and (7) A with B and with C. As used herein, the phrase "at least one of A and B" is intended to refer to any combination or subset of A and B such as (1) at least one A, (2) at least one B, and (3) at least one A and at least one B. Similarly, the phrase "at least one of A or B" is intended to refer to any combination or subset of A and B such as (1) at least one A, (2) at least one B, and (3) at least one A and at least one B.

Moreover, in the foregoing specification, specific embodiments have been described. However, one of ordinary skill in the art appreciates that various modifications and changes can be made in view of aspects of this disclosure without departing from the scope of the invention as set forth in the claims below. Accordingly, the specification and figures are to be regarded in an illustrative rather than a restrictive sense, and all such modifications made in view of aspects of this disclosure are intended to be included within the scope of present aspects.

Additionally, the benefits, advantages, solutions to problems, and any element(s) that may cause any benefit, advantage, or solution to occur or become more pronounced are not to be construed as a critical, required, or essential features or elements of any or all the claims.

Furthermore, although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

Finally, any references, including, but not limited to, publications, patent applications, and patents cited herein are hereby incorporated in their entirety by reference to the same extent as if each reference were individually and specifically indicated to be incorporated by reference and were set forth in its entirety herein.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. A computer-implemented method, executed by one or more processors, to process a medical prescription order rejection, the method comprising:

submitting, using one or more processors via an order handling module, a first order for a medical prescription to a third-party entity for payment; and when a rejection of the first order is received from the third-party entity:

processing, with a trained machine learning model, an input vector including data from the first order and data from the rejection of the first order to form a second order for the medical prescription, wherein the machine learning model is trained by one or more processors via a training module by updating, via the training module, coefficients of the machine learning model based on computed differences of training data representing a plurality of rejected orders and a plurality of approved orders for prescriptions between (i) orders for medical prescriptions determined by the machine learning model, and (ii) associated approved and/or rejected orders; and submitting, using the one or more processors via the order handling module, the second order for the medical prescription to the third-party entity for payment.

2. The method of claim 1, wherein processing, with the trained machine learning model, the first order includes:

processing, with the trained machine learning model, data from the first order and data from the rejection of the first order.

3. The method of claim 2, wherein the data from the rejection of the first order indicates a reason the first order was rejected.

4. The method of claim 1, further including, prior to forming the second order for the medical prescription: applying a plurality of rules to the first order to form a third order for the medical prescription; and submitting the third order for the medical prescription to the third-party entity for payment, wherein the first order is processed with the machine learning model to form the second order when the third order is rejected by the third-party entity.

5. The method of claim 1, further including:

when the second order is approved by the third-party entity, notifying a prescription fulfillment entity that the medical prescription is available to be fulfilled.

6. The method of claim 1, further including:

when the second order for the medical prescription is rejected, submitting the first order for manual review.

7. The method of claim 1, further comprising:

training the machine learning model with a first portion of the training data; and validating the machine learning model with a second portion of the training data.

8. A prescription filler system, the system comprising:

a first interface configured to receive a medical prescription;

a second interface configured to submit via an order handling module a first order for the medical prescription to a third-party entity for approval; and a machine learning model configured and trained to, when the first order is rejected by the third-party entity, process an input vector including data from the first order and data from the rejection of the first order to form a second order for the medical prescription, wherein the second interface is configured to submit the second order via the order handling module for the medical prescription to the third-party entity for payment, and wherein the machine learning model is trained by one or more processors via a training module by updating, via the training module, coefficients of the machine learning model based on computed differences of training data representing a plurality of rejected orders and a plurality of approved orders for prescriptions between (i) orders for medical prescriptions determined by the machine learning model, and (ii) associated approved and/or rejected orders.

9. The prescription filler system of claim 8, wherein the first interface includes the second interface.

10. The prescription filler system of claim 8, wherein, to process the first order, the machine learning model is configured to:

process data from the first order and data from the rejection of the first order.

11. The prescription filler system of claim 10, wherein the data from the rejection of the first order indicates a reason the first order was rejected.

12. The prescription filler system of claim 8, further including a rules-based handler configured to apply a plurality of rules to the first order to form a third order for the medical prescription, wherein the second interface is configured to submit the third order for the medical prescription to the third-party entity for payment, and wherein the first order is processed with the machine learning model to form the second order when the third order is rejected by the third-party entity.

13. The prescription filler system of claim 8, further comprising:

a fulfillment system configured to fill the medical prescription when the second order is approved.

14. The prescription filler system of claim 8, wherein the second interface is further configured to:

when the second order is rejected, submit the first order for manual review.

15. A non-transitory computer-readable storage medium storing instructions that, when executed by one or more processors, cause the one or more processors to:

submit via an order handling module a first order for a medical prescription to a third-party entity for payment; and when a rejection of the first order is received from the third-party entity:

process, with a trained machine learning model, an input vector including data from the first order and data from the rejection of the first order to form a second order for the medical prescription, wherein the machine learning model is trained via a training module by updating, via the training module, coefficients of the machine learning model based on computed differences of training data representing a plurality of rejected orders and a plurality of approved orders for prescriptions between (i) orders for medical prescriptions determined by the machine learning model, and (ii) associated approved and/or rejected orders; and submit via the order handling module the second order for the medical prescription to a third-party entity for payment.

16. The non-transitory computer-readable storage medium of claim 15, wherein the instructions, when executed by the one or more processors, cause the one or more processors to process the first order by:

processing, with the trained machine learning model, data from the first order and data from the rejection of the first order.

17. The non-transitory computer-readable storage medium of claim 16, wherein the data from the rejection of the first order indicates a reason the first order was rejected.

18. The non-transitory computer-readable storage medium of claim 15, including further instructions that, when executed, cause the one or more processors to, prior to forming the second order for the medical prescription:
- apply a plurality of rules to the first order to form a third order for the medical prescription; and
- submit the third order for the medical prescription to the third-party entity for payment,
- wherein the first order is processed with the machine learning model to form the second order when the third order is rejected by the third-party entity.

19. The non-transitory computer-readable storage medium of claim 15, including further instructions that, when executed, cause the one or more processors to, when the second order is approved by the third-party entity, notify a prescription fulfillment entity that the medical prescription is available to be fulfilled.

20. The non-transitory computer-readable storage medium of claim 15, including further instructions that, when executed, cause the one or more processors to, when the second order is rejected, submit the first order for manual review.

\* \* \* \* \*